United States Patent [19]

Otsuka et al.

[11] 4,154,760
[45] May 15, 1979

[54] PROCESS FOR CONTROLLING THE TEMPERATURE DURING UREA SYNTHESIS

[75] Inventors: Eiji Otsuka, Fujisawa; Shinji Yoshimura, Tokyo; Kazumichi Kanai, Fujisawa; Shigeru Inoue, Kamakura, all of Japan

[73] Assignee: Mitsui Toatsu Chemicals, Inc., Tokyo, Japan

[21] Appl. No.: 763,148

[22] Filed: Jan. 27, 1977

Related U.S. Application Data

[63] Continuation of Ser. No. 582,169, May 30, 1975, abandoned, which is a continuation of Ser. No. 38,362, May 19, 1970, abandoned.

[30] Foreign Application Priority Data

Jun. 11, 1969 [JP] Japan .................................. 44-45395
Sep. 10, 1969 [JP] Japan .................................. 44-71237

[51] Int. Cl.² ........................................ C07C 126/02
[52] U.S. Cl. .................................................. 260/555 A
[58] Field of Search ........................ 260/355 A, 555 R; 423/659 E, 659 G

[56] References Cited

U.S. PATENT DOCUMENTS

| | | | |
|---|---|---|---|
| 3,105,093 | 9/1963 | Rothkrans | 260/555 A |
| 3,172,911 | 3/1965 | Mavrovic | 260/555 A |
| 3,270,051 | 8/1966 | Braun | 260/555 A |
| 3,356,723 | 12/1967 | Kaasenbrood | 260/555 A |
| 3,544,628 | 12/1970 | Hsu | 260/555 A |
| 3,636,106 | 1/1972 | Villiers-Fisher | 260/555 A |

FOREIGN PATENT DOCUMENTS 2026608 12/1970 Fed. Rep. of Germany ...... 260/555 A

Primary Examiner—O. R. Vertiz
Assistant Examiner—Thomas W. Roy
Attorney, Agent, or Firm—Fisher, Christen & Sabol

[57] ABSTRACT

A urea synthesis process for converting ammonia and carbon dioxide to urea is improved by providing an easy means of maintaining the urea synthesis zone in the process at a constant temperature. In the process the starting $CO_2$ and up to and including 100 percent of the starting $NH_3$ are reacted in a heat-recovery zone maintained at a urea synthesis pressure. Some of the heat of reaction is removed. The molar ratio of $NH_3$ to $CO_2$ which is fed into the heat-recovery zone is less than 4. The reaction mixture and the rest of the starting $NH_3$ are fed into a urea synthesis zone maintained at urea synthesis pressure to produce urea. The improvement involves adjusting the amount of starting ammonia which is fed into the urea synthesis zone in response to any change in the temperature in the urea synthesis zone so that the urea synthesis zone is maintained at a substantially fixed temperature.

3 Claims, No Drawings

PROCESS FOR CONTROLLING THE TEMPERATURE DURING UREA SYNTHESIS

This is a continuation of application Ser. No. 582,169, filed May 30, 1975, now abandoned, which is a continuation of application Ser. No. 38,362 filed May 19, 1970, now abandoned.

BACKGROUND OF THE INVENTION (a) Field of the Invention

This invention relates to the synthesis of urea and more particularly to an improved method for maintaining the temperature in a urea synthesis autoclave at a constant level.

(b) Prior Art

Urea is used extensively as a fertilizer and in fertilizer formulations. Commercial synthesis of urea is from dry carbon dioxide and ammonia. Under temperature and pressure, ammonia adds to one of the double bonds of the carbon dioxide to yield carbamic acid, which reacts with a second molecule of ammonium to form ammonium carbamate. The generalized reversible equation is:

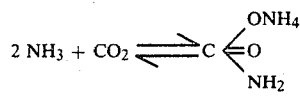

Under pressure and temperature the ammonium carbamate simultaneously converts to urea and water. An excess of ammonia is present. The generalized reversible equation is:

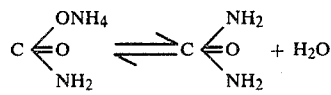

The urea synthesis effluent leaving a urea synthesis autoclave contains urea, water and unreacted ammonium carbamate and excess ammonia, if used. The urea synthesis effluent is subjected to pressure distillation to separate therefrom the unreacted ammonium carbamate (plus excess ammonia) in the form of a gaseous mixture of ammonia and carbon dioxide. The gaseous mixture is absorbed in an absorbent such as water and an aqueous solution of urea to form a recycle solution to be recirculated into the urea synthesis autoclave. In prior art processes, the temperature of the ammonia and recycle solution fed into the urea synthesis autoclave tends to be higher with time as the process of recovering unreacted ammonia and carbon dioxide progesses. As it is desirable to have the synthesis autoclave as a vessel for maintaining the dwelling time, temperature and pressure at any suitable level in order to attain any desired conversion ratio, the relentless increase with time of the quantity of heat in the synthesis autoclave becomes excessive and undesirable. As a result partly gasified ammonia and carbon dioxide leaves the synthesis autoclave, and the conversion ratio consequently falls. The problem is to remove the excess heat of reaction by suitable means whereby the amount of the gaseous ammonia and carbon dioxide leaving the synthesis autoclave is reduced and the decrease of the conversion ratio is avoided. The normal method of removing such excess heat of reaction is to place a heat-recovery device in front of the urea synthesis autoclave. In that method the outlet temperature of the synthesis autoclave is controlled by controlling the recovered heat quantity. In that case the temperature of the heat recovering device is reduced. Consequently, a larger heat-transfer area is required in order to obtain the same steam generation. Also, the urea producing velocity is reduced, which means that the urea synthesis ratio becomes undersirably small.

In two-stage synthesis of urea the temperature of the second stage is often controlled by introducing a part of the carbon dioxide and all of the ammonia into the first stage and introducing the rest of the carbon dioxide into the second stage as disclosed in U.S. Pat. No. 3,105,093, particularily the prior art section thereof. Temperature control is achieved by varying the amount of carbon dioxide introduced into the second stage. However, that method of controlling the temperature has very poor adjustment sensitivity. Also, the opening of the controlling valve used to adjust the carbon dioxide quickly clogs.

Rothkrans discloses in the specification of U.S. Pat. No. 3,105,093 a method for controlling the temperature in the urea synthesis zone, where all of the CO$_2$ and NH$_3$ is introduced into the heat-exchange zone, and the amount of heat removed in the heat-exchange zone is regulated by continuously controlling the pressure of steam generated in the heat-exchange zone in response to the temperature of the urea synthesis zone. However this method involves the disadvantages that the temperature and pressure of the steam generated upon heat recovery in the heat-exchange zone varies with the temperature control, and that such variation is unfavorable when the steam is used for other heating purposes.

The known methods of controlling the temperature in the urea synthesis zone suffer from a number of defects and do not actually achieve such temperature control.

BROAD DESCRIPTION OF THE INVENTION

This invention involves a process for synthesizing urea from carbon dioxide and ammonia. In the process, the carbon dioxide and up to and including 100 percent by weight of the ammonia are reacted in a heat-recovery zone maintained at urea synthesis pressure to form a reaction mixture containing ammonium carbamate. A portion of the heat of reaction produced in the heat-recovery zone is removed. The molar ratio of ammonia to carbon dioxide which is fed into the heat-recovery zone is less than 4. The reaction mixture and any remaining portion of the ammonia are fed into a urea synthesis zone maintained at urea synthesis pressure to form urea. Urea synthesis pressure is normally between 120 and 360 kg./cm$^2$., and preferably is between 150 and 300 kg./cm$^2$. This invention further involves adjusting the temperatures and the amounts of the ammonia which is fed into the urea synthesis zone and the heat-recovery zone in response to any change in the temperature in the urea synthesis zone, so that the urea synthesis zone is maintained at a substantially constant temperature. The temperature used in the urea synthesis zone is normally between 150° and 225° C. and is preferably between 185° and 200° C.

This invention is based upon the fact that in a heat-recovery device for removing the heat of formation of ammonium carbamate from ammonia and carbon dioxide, where, for example, the molar ratio of ammonia to feed carbon dioxide is gradually reduced from 4 to, say, 2.6 and where steam is generated by the heat-recovery zone operation using a constant pressure in the process, the temperature difference between the urea product stream from the urea synthesis zone and the generated steam becomes larger with the reduction of the molar ratio. But the amount of steam generated becomes larger at a greater rate than that expected from the reduction of the molar ratio. For example, when the molar ratio is varied and the temperature difference became 1.1 times as large, the amount of steam generated was 1.3 to 1.4 times as large. This is surprising and it is felt that this result is obtained because the so-called heat transfer coefficient is made larger by the synergistic action of the effect of the mass-transfer and the effect of the heat-transfer on the heat-transfer surface. It is possible to control the amount of steam generated by adjusting the molar ratio, and the variation of the amount of steam generated by the variation of the molar ratio is accurate, repeatable, sensitive enough and yet not too sensitive for process control adjustments, etc.

In case the molar ratio of ammonia to carbon dioxide is in the range of 2 to 4, the amount of the ammonia introduced directly into the urea synthesis autoclave (zone) is decreased and the amount of the ammonia introduced into the heat-recovery zone is increased when the temperature of the urea synthesis zone has decreased due to any cause. When such measures are taken, the molar ratio of ammonia to carbon dioxide in the heat-recovery zone increases and the temperature of the heat-recovery zone decreases. As a result, the amount of steam generated decreases and the temperature of the urea synthesis zone increases. When the molar ratio of ammonia to carbon dioxide in the heat-recovery zone is increased by 0.1, while keeping the ammonia preheating temperature constant, the temperature of the urea synthesis autoclave rises by about 1° C. In the opposite case where the temperature of the urea synthesis zone has risen, the amount of the ammonia introduced into the heat-recovery zone is decreased and, through a process reverse to that described above, the temperature of the urea synthesis zone is reduced.

When the molar ratio of ammonia to carbon dioxide is 2 or less, the whole amount of the starting carbon dioxide is not converted to ammonium carbamate. Therefore, the free carbon dioxide is reacted in the urea synthesis zone with the rest of the starting ammonia fed thereinto to form ammonium carbamate which is then converted, together with the ammonium carbamate from the heat-recovery zone, to urea. Since the reaction for the formation of ammonium carbamate is an exothermic reaction, the temperature of the urea synthesis zone changes according to the quantity of the free carbon dioxide introduced into the zone. The quantity of the free carbon dioxide entering from the heat-recovery zone to the urea synthesis zone is controlled by adjusting the molar ratio of ammonia to carbon dioxide and reacting them under conditions where there is total or partial removal of the heat of the reaction from forming ammonium carbamate. Thus, the molar ratio of ammonia to carbon dioxide in the heat-recovery zone naturally depends upon determination of the temperature upon charging the starting materials into the heat-recovery zone or the urea synthesis zone, and upon the pressure and temperature desired for the operation in the urea synthesis zone. The temperature of the urea synthesis zone is maintained at a definite value by controlling the amount of ammonia introduced into the heat-recovery zone in response to the change in the temperature of the urea synthesizing zone caused by some reason. When the temperature of the urea synthesizing zone is elevated, decrease of the amount of the starting ammonia to be directly introduced into the urea synthesis zone, or, in other words, increase of the amount of ammonia to be introduced into the heat-recovery zone, results in an increase of the amount of ammonium carbamate formed and the necessary removal of heat of the reaction in the heat-recovery zone, thus permitting a decrease of the temperature of the urea synthesizing zone to the desired value. On the contrary, when the temperature of the urea synthesis zone is dropped, increase of the amount of the strating ammonia directly introduced into the urea synthesis zone, or, in other words, decrease of the amount of ammonia introduced into the heat-recovery zone results in an decrease of the amount of ammonium carbamate formed in the heat-recovery zone, with the result that the temperature returns to the desired value. The latter can also be stated to mean there is an increase of the amount of the free carbon dioxide introduced into the urea synthesizing zone and of ammonium carbamate formed therein, thereby raising the temperature to the desired value. The amount of ammonia to be introduced directly into the urea synthesis zone can be controlled manually or by an automatic control system in response to change in the temperature at the exit of the urea synthesis zone.

This invention also involves separation and recovery of unreacted ammonium carbamate contained in the urea product stream and recycling of the recovered ammonium carbamate to the heat-recovery zone or the urea synthesis zone. When the unreacted ammonium carbamate is recycled in the form of an aqueous solution, it may be recycled to either the heat-recovery zone or the urea synthesis zone. In case the recovered ammonium carbamate is recycled to the heat-recovery zone, freshly supplied carbon dioxide alone can be introduced thereinto intermittently in an amount necessary for controlling the temperature of the urea synthesizing zone. As the ammonium carbamate solution in that case usually contains excess ammonia, introduction of such fresh carbon dioxide alone permits the formation of ammonium carbamate and evolution of the heat of the formation.

In case the unreacted ammonium carbamate is recycled in the form of a gaseous mixture with ammonia and carbon dioxide, it is introduced together with a freshly supplied carbon dioxide and, if necessary, newly supplied ammonia into the heat-recovery zone wherein the whole is brought to reaction under pressure and a part of heat of the reaction is recovered. The unreacted ammonium carbamate in the urea product stream is stripped under a urea synthesis pressure or a lower pressure with the freshly supplied carbon dioxide, and the resulting gaseous mixture of ammonia and carbon dioxide may be recycled to the heat-recovery zone. In this case, it is of course possible, when necessary, to introduce the freshly supplied ammonia into the heat-recovery zone.

The upper limit of the range of the molar ratio of ammonia to carbon dioxide in the ammonium carbamate-producing zone (heat-recovery zone) is 4 and the lower limit is preferably one. When the molar ratio of ammonia to carbon dioxide is more than 4, the temperature response of the urea synthesis autoclave is not as sensitive as in the case of a molar ratio of 1.4 to 3, which is the preferred $NH_3/CO_2$ molar ratio range.

DETAILED DESCRIPTION OF THE INVENTION

In the drawing:

The FIGURE is a flow diagram of the preferred embodiment of this invention.

The preferred process of this invention is explained in accordance with the flow diagram of the FIGURE.

Liquid ammonia under a urea synthesis pressure, for example, a gauge pressure of about 150 to 300 kg./cm$^2$. is introduced into ammonia preheater 2 through pressure line 1. The pressurized liquid ammonia is preheated to a temperature of about 80° to 160° C. by means of high pressure steam introduced into heater 3. Part or all of the preheated ammonia is introduced into heat-recovery device (ammonium carbamate producing zone) 7 through process line 4. Into heat-recovery device 7 are introduced carbon dioxide pressurized to a urea synthesis pressure and a recycle solution containing the recovered unreacted ammonium carbamate (unreacted substance) from unreacted-substance-recovering step 15 through lines 5 and 6, respectively. The unreacted substance may not be recirculated at all, or the unreacted material may not be recirculated in the form of a solution, in which case there will be no recycle solution. For example, the unreacted substance in the form of a gaseous mixture may be introduced directly into urea synthesis device 12 as a compressed gas. The molar ratio of $NH_3/CO_2$ of the free ammonia and the free carbon dioxide from any source which is introduced into heat recovering device 7 is kept at leas than 4. This is done to keep the heat-transfer area in heat-recovery device 7 in a desirable range by increasing the heat-transfer coefficient. (Heat recovery device 7 can be replaced by any appropriate method whereby the excess calories are recovered.)

In heat-recovery device 7, due to the heat of reaction from the production of ammonium carbamate, the temperature reaches between about 175° and 190° C. Heat may be recovered by introducing the urea synthesis effluent, having its pressure reduced, for example, zero to 100 kg./cm$^2$ gauge pressure, through line 8, and making it indirectly exchange heat with the reaction mixture to decompose the unreacted ammonium carbamate. Or, water may be introduced through the line 8 to generate steam having a gauge pressure of 3 to 6 kg./cm$^2$. The amount of heat-recovery is naturally determined by the adjustment of the amount of the ammonia introduced directly into urea synthesis autoclave 12. The temperature of urea synthesis autoclave 12 is kept at any desired value, e.g., about 150° to about 225° C., and the pressure of urea synthesis autoclave is kept at any desired value, e.g., about 120 to about 360 kg./cm$^2$. (gauge pressure).

Part or all of the ammonia from ammonia preheater 2 is passed through controlling valve 9 and process line 10 and is introduced into urea synthesis autoclave 12 via pressure line 11 together with the reaction mixture from heat-recovery device 7. Controlling valve 9 can be operated, for example, by a servomotor in response to the outlet temperature of urea synthesis autoclave 12 in order (a) to control the amount of the ammonia introduced directly into urea synthesis autoclave 12 and (b) to control the amount of the ammonia introduced into heat-recovery device 7 through process line 4. The result is the adjustment of the outlet temperature of urea synthesis autoclave 12 to a definite value. The outlet temperature of urea synthesis autoclave is preferably kept at about 160° to 200° C. The urea synthesis effluent from urea synthesis autoclave 12 is fed to an unreacted substance recovery step 15 through pressure reduction valve 13 (which may be omitted in some cases) and process line 14, and urea is recovered via line 16. The unreacted substance can be recirculated to heat-recovering device 7 as a recycle solution via line 6.

According to the present invention, by adjusting the amount of the ammonia introduced directly into the urea synthesis autoclave, the performance of the heat recovering device is improved. Also, the temperature of the urea synthesis autoclave can be sensitively kept at a fixed value by varying the amount of heat recovered in response to the variation of the temperature of the synthesis autoclave. This is a great advantage when compared with the conventional, relatively non-sensitive method of adjusting the temperature of the urea synthesis autoclave by varying the amount of heat recovered only by the variation of the temperature difference. Further, the problem of clogging the opening of a carbon dioxide-controlling valve as used in one of the conventional method of adjusting the temperature of the urea synthesis autoclave by adjusting the amount of carbon dioxide, is avoided by the present invention because only liquid ammonia is passed through a control valve.

Unless otherwise stated or indicated, in the following example, all percentages and proportions are expressed on a weight basis. The following examples further illustrate, but do not limit, this invention.

EXAMPLE I 120 kg./hr. of gaseous carbon dioxide (line 5) and 175 kg./hr. of a recycle solution (line 6) having a temperature of 95° C. and having a composition of 36% ammonia, 30% $CO_3$. 16% urea and 18% water, were each separately pressurized to a gauge pressure of 200 kg./cm$^2$. 224 kg./hr. of liquid ammonia (at 35° C.) was passed through preheater 2 wherein it was preheated to 150° C. using the steam that had been previously used in the step of separating the unreacted substance from the urea in product stream (line 14) coming from urea synthesizing device 12. 112 kg./hr. of the preheated ammonia (line 10) was fed directly into urea synthesis autoclave 12 and 112 kg./hr. of the preheated ammonia (line 4) was fed, together with the above-mentioned carbon dioxide and recycle solution into heat-recovery device 7. The molar ratio of $NH_3/CO_2$ in the heat-recovery device at that time was 2.6. The temperature of the liquid in the inlet mixing part of heat-recovery device 7 reached 182° C. and the outlet temperature was the same. The amount of heat recovered was 25 kg./hr. of steam having a gauge pressure of 3 kg./cm$^2$. The reaction mixture (line 11) from heat-recovery device 7 was introduced into urea synthesis autoclave 12. The outlet temperature of urea synthesis autoclave 12 reached 194° C. and the urea synthesis rate was 72%. The outlet temperature of urea synthesis autoclave 12 was kept at 194° C. by adjusting the amount of the ammonia introduced directly into urea synthesis autoclave 12 so that the increase of the molar ratio of $NH_3/CO_2$ by 0.1 in heat-recovery device 7 would cause the temperature of urea synthesis autoclave 12 to rise by 1° C. (This ratio to temperature relationship is only a guide). When the temperature of the preheated ammonia was 132.5° C., in order to keep the same outlet temperature of 194° C. for autoclave 12, it was necessary to feed all the amount of the ammonia (line 1) into heat-recovery device 7. The temperature of the liquid in the inlet mixing part of heat-recovery device 7 dropped to 178° C. and the amount of generated steam was 17 kg./hr. Further, when the preheated ammonia temperature was 90° C., the greater part of the ammonia (line 1) was fed directly into urea synthesis autoclave 12. When the molar ratio of $NH_3/CO_2$ in the heat-recovery device became 1.7, the outlet temperature of urea synthesis autoclave 12 being kept at 194° C., the amount of steam generation was 5.0 kg./hr.

EXAMPLE II 120 kg./hr. of gaseous carbon dioxide (line 5), and 175 kg./hr. of a recycle solution (line 6) at 113° C. were each separately pressurized to a gauge pressure of 250 kg./cm². The recycle solution had a composition of 36% ammonia, 30% $CO_2$, 16% urea and 18% water. 224 kg./hr. of liquid ammonia (at 35° C.) was passed through preheater 2 wherein it was preheated to 150° C. using the steam that had been previously used in the step of separating the unreacted substances from the urea in the product stream (line 14) coming from autoclave 12. 112 kg./hr. of the preheated ammonia (line 10) was introduced directly into urea synthesis autoclave 12 and 112 kg./hr. of the preheated ammonia (line 4) was fed, together with the abovementioned carbon dioxide and recycle solution, into heat-recovery device 7. The molar ratio of $NH_3/CO_2$ in the heat-recovery device at that time was 2.6. The temperature of the liquid in the inlet mixing part of the heat-recovery device reached 190° C. and the outlet temperature was the same. The amount of heat recovered then was 27.5 kg./hr. of steam having a gauge pressure of 3 kg./cm²·. The reaction mixture (line 11) from heat-recovery device 7 was introduced into urea synthesis autoclave 12. The outlet temperature of urea synthesis autoclave 12 reached 197° C. and the urea synthesis rate was 74%. The outlet temperature of urea synthesis autoclave 12 was kept at 197° C. by adjusting the amount of ammonia introduced directly into urea synthesis autoclave 12 so that the molar ratio of $NH_3/CO_2$ in heat recovering device 7 was 3.3 when the temperature of the preheated ammonia was reduced to 142° C. The amount of steam generated was 23.8 kg./hr. When the temperature of the preheated ammonia was 136° C., in order to keep the same outlet temperature of 197° C. for autoclave 12, it was necessary to feed all the amount of the ammonia into heat-recovery device 7. The temperature of the liquid in the inlet mixing part of heat-recovery device 7 dropped to 185° C., and the amount of generated steam was 21.1 kg./hr. Further, when the preheated ammonia temperature was 100° C., the greater part of the ammonia was fed directly into urea synthesis autoclave 12. When the molar ratio of $NH_3/CO_2$ in heat-recovery device 7 became 1.6, the outlet temperature of urea synthesis autoclave 12 being kept at 197° C., the amount of steam generated was 5.3 kg./hr. This example demonstrates the same principle shown in Example I.

EXAMPLE III 120 kg./hr. of gaseous carbon dioxide (line 5), and 175 kg./hr. of a recycle solution (line 6) having a temperature of 95° C. and having a composition of 36% ammonia, 30% carbon dioxide, 16% urea and 18% water were each separately pressured to a gauge pressure of 200 kg./cm². 224 kg./hr. of liquid ammonia (at 35° C.) was passed through preheater 2 wherein it was preheated to 90° C. using the steam that had been previously used in the step of separating the unreacted substances from the urea in the product stream (line 14) coming from urea synthesizing device 12. 176 kg./hr. of the preheated ammonia (line 10) was introduced directly into autoclave 12 and 48 kg./hr. of the preheated ammonia (line 4) was introduced, together with the above-mentioned carbon dioxide and recycle solution, into heat-recovery device 7. The molar ratio of $NH_3/CO_2$ in heat-recovery device 7 was 1.7. The temperature of the liquid in the inlet mixing part of heat-recovery device 7 reached 170° C. and the outlet temperature of device 7 was the same. The amount of heat-recovered at that time was 5 kg./hr. of steam having a gauge pressure of 3 kg./cm³. The reaction mixture (line 11) descharged from heat-recovery device 7 was introduced into urea synthesis autoclave 12. The outlet temperature of urea synthesis autoclave 12 reached 194° C. and the urea conversion (synthesis) ratio was 72%. When the temperature of urea synthesis autoclave 12 rose by 5° C., the exit temperature of urea autoclave 12 was reduced to and maintained at 194° C. by increasing the molar ratio of $NH_3/CO_2$ in heat-recovery device 12 to 1.74. The amount of steam evolved at that time was 10.1 kg./hr.

EXAMPLE IV 120 kg./hr. of gaseous carbon dioxide, and 175 kg./hr. of a recycle solution (line 6) having a temperature of 113° C. and having a composition of 36% ammonia, 30% carbon dioxide, 16% urea and 18% water, were each separately pressurized to a gauge pressure of 250 kg./cm². 224 kg./hr. of liquid ammonia (at 35° C.) was passed through preheater 2 wherein it was preheated to 100° C. using the steam that had been previously used in the step of separating the unreacted substances from the urea in the product stream (line 14) coming from urea synthesizing device 12. 183 kg./hr. of the preheated liquid ammonia (line 10) was introduced directly into the urea synthesis autoclave, and 41 kg./hr. of the preheated liquid ammonia was introduced, together with the above-mentioned carbon dioxide and recycle solution, into the heat-recovery device. The molar ratio of $NH_3/CO_2$ in the heat-recovery device at that time was 1.6. The temperature of the liquid in the inlet mixing part of heat-recovery device 7 was 177° C. and the outlet temperature of the device as the same. The amount of heat recovered at that time was 5.3 kg./hr. of steam having a gauge pressure of 3 kg./cm². The reaction mixture (line 11) discharged from heat-recovery device 7 was fed to urea synthesis autoclave 12, whereupon the temperature at the exit of the synthesis autoclave went to 197° C. and the conversion ratio was 74%. When the temperature of the preheated ammonia was raised to 140° C., the temperature at the exit of urea synthesis autoclave 12 could be maintained at 197° C. by adjusting the amount of ammonia directly introduced into autoclave 12 so that the molar ratio of $NH_3/CO_2$ in heat-recovery device 7 was raised to 1.76. The amount of steam evolved at that time was 24.6 kg./hr. This example demonstrates that when the ammonia is preheated to a higher temperature, the urea synthesis zone temperature can be maintained by raising the $NH_3/CO_2$ molar ratio in the heat-recovery zone.

What is claimed is:

1. In a process for synthesizing urea from carbon dioxide and ammonia which comprises feeding to and reacting in a heat-recovery zone maintained at urea synthesis pressure all of said carbon dioxide and a part of said ammonia to form a reaction containing ammonium carbamate, the molar ratio of ammonia to carbon dioxide which is fed to said heat-recovery zone being in the range 2:1 to 4:1, removing all of or some portion of the heat of reaction produced in said heat-recovery zone by means of indirect heat exchange, and feeding said reaction mixture and remaining amount of said ammonia into a urea synthesis zone maintained at urea synthesis pressure and at a temperature of 150° C. to 225° C. to form urea, the improvement comprising maintaining the outlet temperature of said urea synthesis zone at a substantially constant value by adjusting the relative amounts of ammonia fed into said heat-recovery zone and said urea synthesis zone, so that when said outlet temperature of said urea synthesis zone begins to increase, said constant temperature is maintained by decreasing the amount of ammonia fed into said heat-recovery zone, and when said outlet temperature of said urea synthesis zone begins to decrease, said constant temperature is recovered by increasing the amount of ammonia fed into said heat-recovery zone.

2. A process as described in claim 1 wherein said ammonia is heated to a temperature between 80° and 160° C. prior to being fed into said heat-recovery zone or said urea synthesis zone.

3. A process as described in claim 1 wherein the outlet temperature of said urea synthesis zone is maintained at a temperature between 185° and 200° C., and wherein said urea synthesis pressure is a gauge pressure between 150 and 300 kg./cm$^2$.

* * * * *